US009990552B2

(12) United States Patent
Melas et al.

(10) Patent No.: US 9,990,552 B2
(45) Date of Patent: Jun. 5, 2018

(54) OPERATOR FATIGUE MONITORING SYSTEM

(71) Applicant: Electro-Motive Diesel, Inc., LaGrange, IL (US)

(72) Inventors: Dennis John Melas, Chicago, IL (US); John David Semple, Woodridge, IL (US)

(73) Assignee: Progress Rail Locomotive Inc., LaGrange, IL (US)

( * ) Notice: Subject to any disclaimer, the term of this patent is extended or adjusted under 35 U.S.C. 154(b) by 0 days. days.

(21) Appl. No.: 14/820,281

(22) Filed: Aug. 6, 2015

(65) Prior Publication Data

US 2016/0082838 A1    Mar. 24, 2016

Related U.S. Application Data

(60) Provisional application No. 62/053,164, filed on Sep. 21, 2014.

(51) Int. Cl.
*G08B 23/00* (2006.01)
*G08B 17/12* (2006.01)
*G06K 9/00* (2006.01)
*A61B 5/18* (2006.01)
*A61B 5/11* (2006.01)

(52) U.S. Cl.
CPC ............ *G06K 9/00845* (2013.01); *A61B 5/18* (2013.01); *A61B 5/1114* (2013.01)

(58) Field of Classification Search
CPC ...... G06K 9/00845; A61B 5/18; A61B 5/1114
USPC ......................................................... 340/575
See application file for complete search history.

(56) References Cited

U.S. PATENT DOCUMENTS

2004/0124985 A1    7/2004  Young et al.
2008/0243389 A1*  10/2008  Inoue .................... G08G 1/165
                                                                 701/301
2010/0188233 A1    7/2010  Kuntzel
(Continued)

FOREIGN PATENT DOCUMENTS

JP    2005-158077 A    6/2005
JP    2013-235341 A    11/2013

OTHER PUBLICATIONS

"Locomotive In-Cab Alerter Technology Assessment" by Man Vehicle Laboratory of the Massachusetts Institute of Technology (Nov. 20, 2006).
(Continued)

*Primary Examiner* — Tanmay Shah
(74) *Attorney, Agent, or Firm* — Finnegan, Henderson, Farabow, Garrett & Dunner, LLP

(57) ABSTRACT

A fatigue monitoring system is disclosed for use with a machine. The fatigue monitoring system may have an input device configured to generate a first signal indicative of an activity performed by a machine operator, a scanning device configured to generate a second signal indicative of a recognized characteristic of the machine operator, and a warning device. The fatigue monitoring system may also have a controller in communication with the input device, the scanning device, and the warning device. The controller may be configured to determine a time between generations of the first signal, to make a comparison of the recognized characteristic with a threshold characteristic, and to selectively activate the warning device based on the time or the comparison.

17 Claims, 4 Drawing Sheets

(56) References Cited

U.S. PATENT DOCUMENTS

| | | | | |
|---|---|---|---|---|
| 2011/0313259 A1* | 12/2011 | Hatakeyama | ............ | A61B 5/18 600/300 |
| 2012/0188376 A1* | 7/2012 | Chatow | ................ | G07C 5/0891 348/148 |
| 2014/0362346 A1* | 12/2014 | Leinonen | ................. | A61B 5/16 351/224 |
| 2015/0038855 A1* | 2/2015 | Berckmans | ........ | A61B 5/02055 600/483 |

OTHER PUBLICATIONS

Charles M. Oman et al., "Locomotive In-Cab Alerter Technology Assessment. Development of Alternative Locomotive In-Cab Alerter Technology." Jul. 30, 2007, pp. 1-28. (http://citeseerx.ist.psu.edu/viewdoc/summary?doi=10.1.1.494.9853).

* cited by examiner

OPERATOR FATIGUE MONITORING SYSTEM

RELATED APPLICATIONS

This application is based on and claims priority to U.S. Provisional Application No. 62/053,164 filed on Sep. 21, 2014, the contents of which are expressly incorporated herein by reference.

TECHNICAL FIELD

The present disclosure relates generally to an operator fatigue monitor system and, more particularly, to a system for monitoring fatigue in operators of a machine such as a train locomotive.

BACKGROUND

Fatigue is a known problem in the transportation industry. Operators can become fatigued after extended periods of time of machine control. Some machines require repetitive movements from the operator that can be tiring, while other machines require very little operator movement that can result in drowsiness. In either situation, the operator may lose some ability to concentrate and the operator's attentiveness may dull. This can result in improper machine control, delayed machine control, or lack of machine control. Any of these results can cause a loss in productivity, profitability, and safety.

One exemplary system for helping an operator stay alert is commonly known as a vigilance control device. A vigilance control device includes lights and sounders that are connected to timers. The operator is required to provide some type of input with a minimum frequency that is controlled by the timers. If the input is not received within a particular time period, a warning in the form of a flashing light or a sounding siren is initiated. If the operator still does not provide any input, the vigilance control device automatically implements a penalty in the form of a machine speed reduction or activation of the machine's brakes. Such a system is described in a publication by the Man Vehicle Laboratory of the Massachusetts Institute of Technology titled "Locomotive In-Cab Alerter Technology Assessment" that published on Nov. 20, 2006 (the "Alerter Publication").

In addition to describing conventional activity-based Alerters, the Alerter Publication also describes a new type of Alerter that automatically detects operator fatigue without operator input. In particular, the automatic Alerter relies on video images of the operator, and uses computer machine vision algorithms to identify specific features in the video images (e.g., head pose, gaze direction, and eyelid position). Based on these features, the automatic Alerter then generates the warnings and/or penalty described above.

While the conventional Alerter and the automatic Alerter may both provide some benefit in keeping an operator vigilant and alert, they both suffer drawbacks. For example, the conventional Alerter has been determined to encourage preemptive behavior that avoids activation of startling warnings. In addition, it has been found that train operators can, over time, become accustomed to providing input to the Alerter as a reflexive activity that does not require concentration and that can even be done while asleep. Further, the automatic Alerter can sometimes misread an operator's face, particular when lighting conditions are poor, when the operator is wearing glasses, or during other similar conditions.

The present disclosure is directed at overcoming one or more of the shortcomings set forth above and/or other problems of the prior art.

SUMMARY

In one aspect, the present disclosure is directed to fatigue monitoring system for a machine. The fatigue monitoring system may include an input device configured to generate a first signal indicative of an activity performed by a machine operator, a scanning device configured to generate a second signal indicative of a recognized characteristic of the machine operator, and a warning device. The fatigue monitoring system may also include a controller in communication with the input device, the scanning device, and the warning device. The controller may be configured to determine a time between generations of the first signal, to make a comparison of the recognized characteristic with a threshold characteristic, and to selectively activate the warning device based on the time or the comparison.

In another aspect, the present disclosure is directed to another fatigue monitoring system for a machine. This fatigue monitoring system may include an input device configured to generate a first signal indicative of an activity performed by a machine operator, a scanning device configured to generate a second signal indicative of a recognized characteristic of the machine operator, a warning device, and a controller in communication with the input device, the scanning device, and the warning device. The controller may be configured to determine a time between generations of the first signal, to selectively implement a first level response when the time between generations of the first signal exceeds a first threshold time, and to selectively implement a second level response when the time between generations of the first signal exceeds a second threshold time greater than the first threshold time. The controller may also be configured to make a comparison of the recognized characteristic with a threshold characteristic, and to selectively implement the second level response based on the comparison.

In yet another aspect, the present disclosure is directed to a method of monitoring fatigue in a machine operator. The method may include receiving inputs indicative of an activity performed by the machine operator, and scanning a facial characteristic of the machine operator. The method may also include determining a time between receipt of the inputs, and making a comparison of the characteristic with a threshold characteristic. The method may further include selectively activating a warning device based on the time or the comparison.

DETAILED DESCRIPTION

Figure 1:
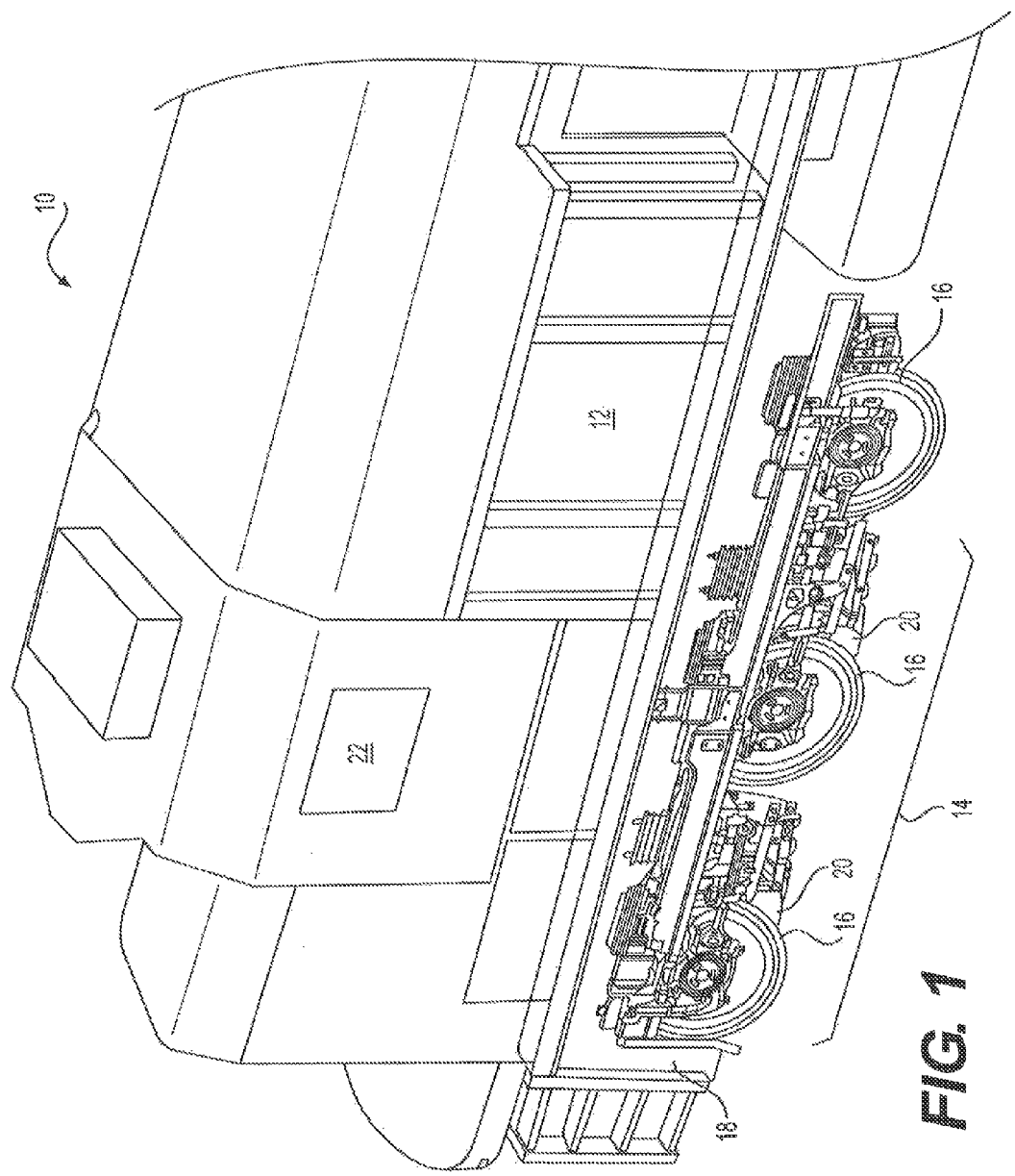
FIG. 1 is an isometric illustration of an exemplary disclosed locomotive.

FIG. 1 illustrates an exemplary mobile machine 10. In the disclosed example, machine 10 is a locomotive. However, it is contemplated that machine 10 may embody another type of machine, if desired. For example, machine 10 may embody an on- or off-highway haul truck, a construction machine, or a vocational vehicle. Alternatively, machine 10 could be a stationary machine, such as a genset, a pump, or a drill that requires continuous attention from an operator. Other types of machines may also be possible.

As a locomotive, machine 10 may include a car body 12 supported at opposing ends by a plurality of trucks 14 (only one truck 14 shown in FIG. 1). Each truck 14 may be configured to engage a track 15 (shown only in FIG. 2) via a plurality of wheels 16, and to support a frame 18 of car body 12. One or more braking devices 20 may be associated with one or all wheels 16 of a particular truck 14, and any number of engines (not shown) may be mounted to frame 18 within car body 12 and drivingly connected to propel wheels 16. Control over wheel braking and engine fueling (as well as other locomotive controls) may be provided by way of an operator cabin 22 that is supported by frame 18.

Figure 2:
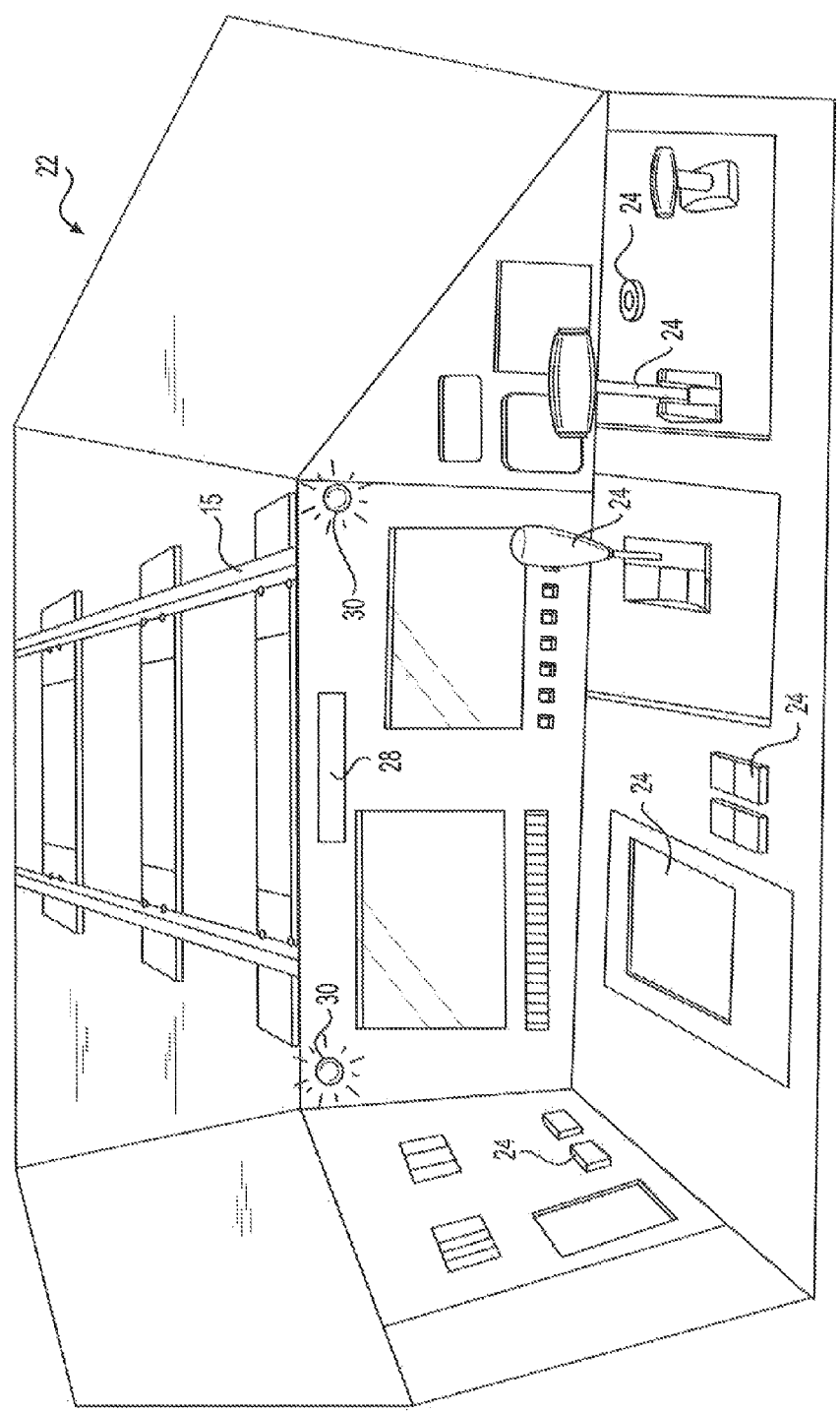
FIG. 2 is an isometric illustration of an exemplary disclosed cabin that may form a portion of the locomotive of FIG. 1.

The interior of an exemplary cabin 22 is shown in FIG. 2. As can be seen in this figure, cabin 22 may house a plurality of input devices 24. Input devices 24 may be used by the operator to control machine 10 and embody any type of device known in the art. For example, input devices 24 may include, among other things, a throttle configured to control fueling of machine 10 and a brake lever configured to control braking of machine 10. Input devices 24 may be levers, pedals, wheels, knobs, push-pull devices, touch screen displays, etc.

In the disclosed embodiment, movements and other activities of a machine operator may be tracked from inside of cabin 22. These movements and/or activities may include the use of input devices 24. For example, in addition to generating control signals used to control machine operations, one or more of the signals generated by input devices 24 may also be monitored and used by a fatigue monitoring system 26 ("system"—shown in FIG. 3) as a way to determine if the operator is fatigued. In particular, based on a frequency of input device use, system 26 may be able to determine if the operator is alert (e.g., when input is received frequently), slightly fatigued (e.g., when input frequency is reduced), significantly fatigued (e.g., when input is sporadically received), or even asleep (e.g., when no input is received). In some embodiments, a dedicated input device 24 may used for this purpose. That is, a particular input device 24 may be provided for the sole purpose of demonstrating operator alertness. The machine operator must manipulate this dedicated input device 24 with a minimum frequency in order to show a desired level of alertness.

In addition to using the frequency of input device 24 use as a way to determine a fatigue level of the machine operator, system 26 may use monitoring hardware for this same purpose. For example, system 26 may include a scanner 28 alone or together with one or more light sources 30. In the disclosed example, scanner 28 is an IR scanner (e.g., a camera) and light sources 30 produce IR light that is only visible to scanner 28 for use by scanner 28 during low-light conditions. Other types of scanners and/or light sources may alternatively be utilized for this purpose, if desired. Scanner 28 and light sources 30 may be located within cabin 22, for example within a central control panel facing the machine operator.

Figure 3:
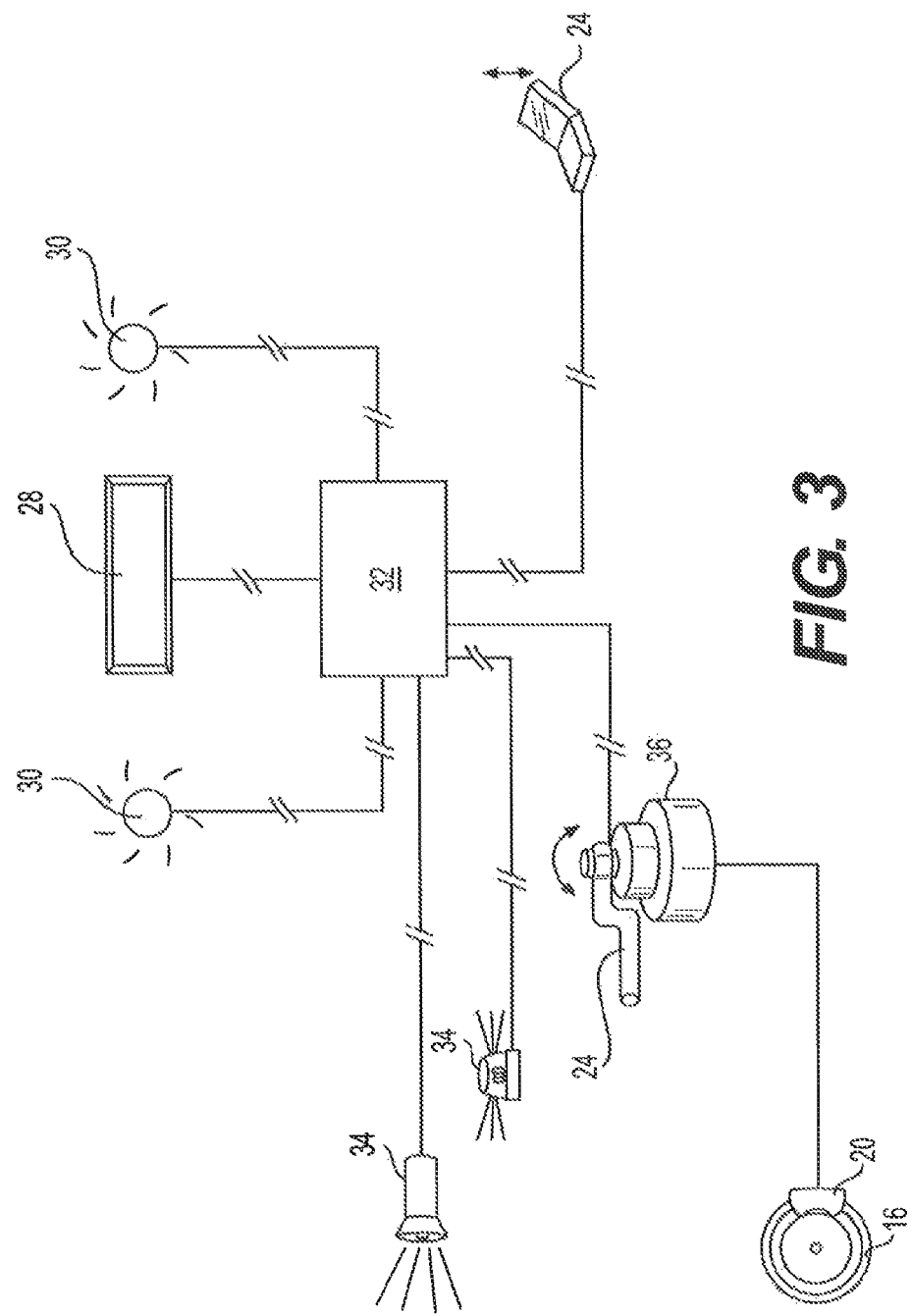
FIG. 3 is a diagrammatic illustration of an exemplary disclosed fatigue monitoring system that may be used in conjunction with the locomotive and cabin of FIGS. 1 and 2.

As shown in FIG. 3, system 26 may include a controller 32 that is in communication with input devices 24, scanner 28, and light sources 30. Controller 32 may be configured to receive signals generated by these components, determine a level of operator fatigue based on the signals, and selectively activate one or more warning devices 34 and/or a penalty device 36. In the disclosed example, two warning devices 34 are shown, including an audible warning device and a visual warning device. It is contemplated that any number and/or type of warning device 34 may be used and located anywhere on machine 10 (e.g., within cabin 22). Penalty device 36 may be a device used by controller 32 to automatically adjust operation of machine 10 when the operator is determined to be fatigued past a threshold amount (e.g., when the operator is unresponsive). In the disclosed example, penalty device 36 is an actuator functional to automatically activate braking device 20 associated with wheels 16. In some embodiments, this same actuator (or another actuator) may be used to simultaneously (or separately) reduce fueling of the engine of machine 10.

Controller 32 may embody a single microprocessor or multiple microprocessors that include a means for controlling operations of machine 10 (e.g., of system 26) in response to received signals. Numerous commercially available microprocessors can be configured to perform the functions of controller 32. It should be appreciated that controller 32 could readily embody a general machine microprocessor capable of controlling numerous machine functions. Controller 32 may include a memory, a secondary storage device, a processor, a timer, and any other components for running an application. Various other circuits may be associated with controller 32 such as power supply circuitry, signal conditioning circuitry, solenoid driver circuitry, and other types of circuitry.

Figure 4:
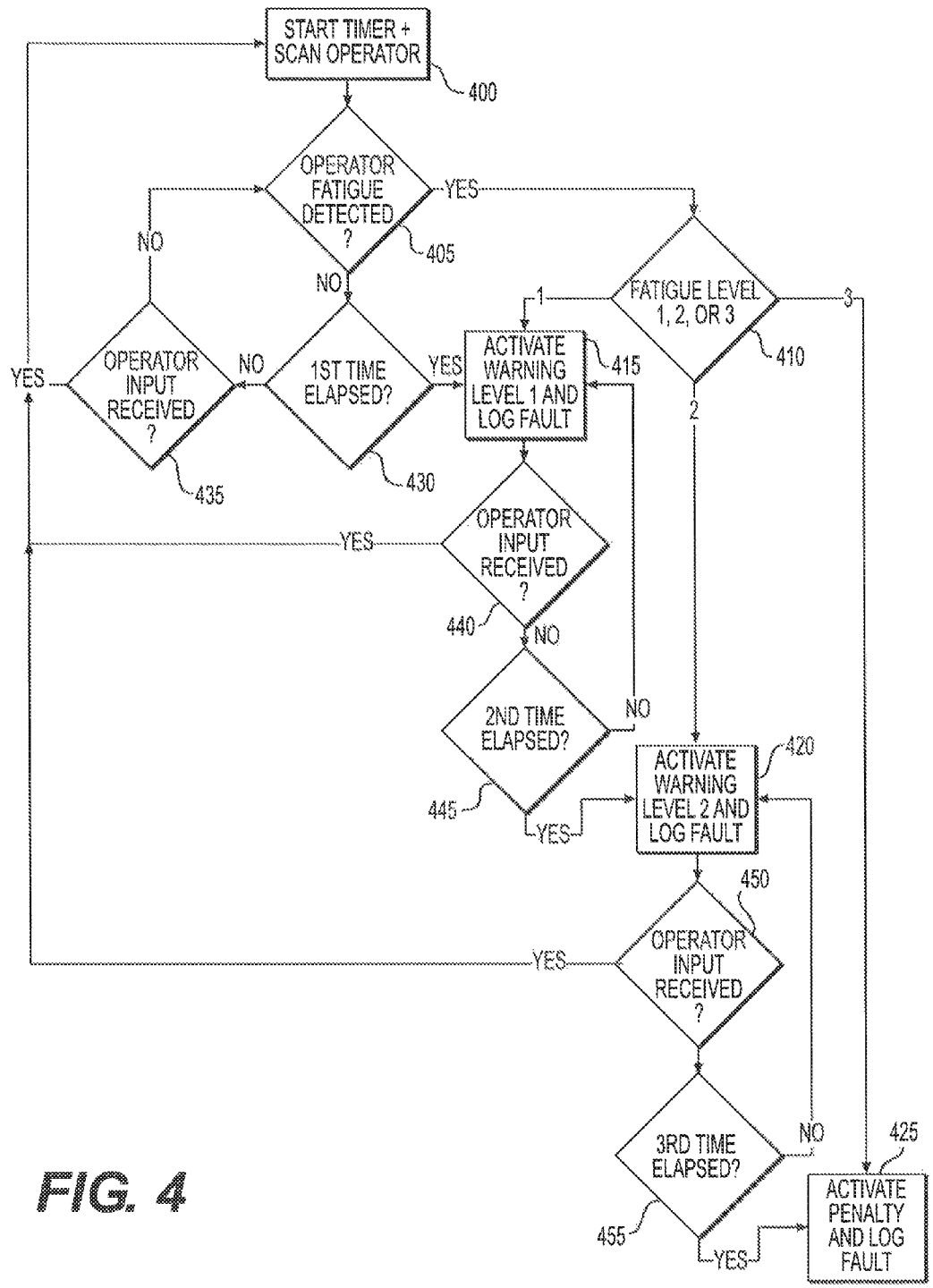
FIG. 4 is a flowchart depicting an exemplary disclosed method that may be performed by the fatigue monitoring system of FIG. 3.

FIG. 4 illustrates an exemplary method performed by controller 32. FIG. 4 will be discussed in detail in the following section to further explain the disclosed concepts.

INDUSTRIAL APPLICABILITY

The fatigue monitoring system of the present disclosure may be applicable to any machine where operator alertness is important. The disclosed fatigue monitoring system may help to keep the operator alert by monitoring an activity level of the operator and also by monitoring characteristics (e.g., facial characteristics) of the operator. When the fatigue monitoring system determines that the operator is fatigued, a level of the fatigue may be judged and multiple different actions may be taken to alert the operator and/or to override operator control and ensure safe machine operation. Operation of fatigue monitoring system 26 will now be described in detail.

During operation of machine 10, system 26 may be used to determine and respond to a fatigue level of the operator. Controller 32 may initiate this process by starting an internal timer and initiating a scan of the operator (Step 400). The scan may be initiated by activating scanner 28 and, in some instances, also activating light sources 30. Based on the images and/or video produced by scanner 28, controller 32 may then determine if the operator is fatigued (Step 405). In particular, controller 32 may compare the scanned image of the operator with one or more images stored in memory. For example, controller 32 may determine an actual head pose from the scanned image, and compare the actual head pose to one or more head poses corresponding to different levels of operator fatigue. In another example, controller 32 may calculate an eye position or eye blink frequency from the scanned image, and compare the eye position and/or blink frequency to threshold positions or frequencies. Other operator characteristics may also or alternatively be captured in the scanned image and compared to information stored in memory corresponding to the different levels of operator fatigue.

Based on these comparisons, controller 32 may then determine if the fatigue level of the operator corresponds with a particular level that requires action by controller 32. For example, controller 32 may determine if the operator is fatigued at a level 1, at a level 2, or at a level 3 (Step 410). In the disclosed embodiment, level 1 fatigue may correspond with a slightly fatigued operator wherein response time and/or judgment may be somewhat impaired. Level 2 fatigue may correspond with a significantly fatigued operator wherein response time and/or judgment is significantly impaired. Level 3 fatigue may correspond with an unresponsive operator (e.g., an operator that has fallen asleep). It is contemplated that any number of fatigue levels may be utilized by system 26, and/or that the levels of fatigue may have different meanings, if desired.

When controller 32 determines, based on the scan of the operator, that the operator is fatigued at level 1, controller 32 may activate warning device 34 at a level 1 output and also log a corresponding fault condition (Step 415). In the disclosed embodiment, the level 1 warning may include activation of only visual warning device 34, with the intention to alert and refresh the operator.

When controller 32 determines, based on the scan of the operator, that the operator is fatigued at level 2, controller 32 may activate warning device 34 at a level 2 output and also log a corresponding fault condition (Step 420). In the disclosed embodiment, the level 2 warning may include activation of only audible warning device 34 or activation of both visual and audible warning devices 34, with the intention to alert and refresh the operator by a greater degree.

When controller 32 determines, based on the scan of the operator, that the operator is fatigued at level 3, controller 32 may activate penalty device 36 and also log a corresponding fault condition (Step 425). In some applications, controller 32 may additionally communicate (e.g., via wireless communications) the fault condition to other personal onboard machine 10 and/or to another location (e.g., to the central service facility). In the disclosed embodiment, activation of penalty device 36 may result in a reduction of engine fueling, activation of braking devices 20, or both, with the intention to override the operator and slow or stop machine 10.

Even if the scan of the operator does not show that the operator is fatigued, the operator could still be fatigued and the fatigue simply not detectable via scanning. Accordingly, if the operator is determined at step 405 to not be fatigued, controller 32 may check the activity level of the operator to determine if a first time threshold has elapsed since input from the operator was received via devices 24 (Step 430). If the first time threshold has not elapsed, controller 32 may determine if any input from the operator has been received (Step 435). When input from the operator is received, the timer may be reset and control may return to step 400. Control may cycle through steps 405, 430, and 435 until the input is received or until the first time threshold has elapsed. In the disclosed embodiment, the first time threshold may be about 45 seconds, although other time thresholds may also be utilized.

If the first time threshold elapses without additional input from the operator, controller 32 may activate the level 1 warning and log the corresponding fault condition (Step 415). Controller 32 may then continue monitoring operator input to determine if the input is subsequently received (Step 440) and also continue providing the warning at level 1. As with step 435 described above, once the input is received, control may pass to step 400 and the timer may be reset. However, if a second time threshold greater than the first time threshold is determined to have elapsed without operator input (Step 445), controller 32 may activate warning device(s) 34 at level 2 and log the corresponding fault condition (Step 420).

Again, controller 32 may monitor operator input after activation of warning devices 34 at level 2 to determine if the input is subsequently received (Step 450), continue tracking time, and continue activation of warning devices 34. As with steps 435 and 440 described above, once the input is received, control may pass to step 400 and the timer may be reset. However, if controller 32 determines that a third time threshold greater than the first time threshold has elapsed without operator input (Step 455), controller 32 may activate penalty device 36, log the fault condition, and/or communicate the log to other personnel or to the offboard service facility (Step 425).

In an alternative embodiment, not shown, controller 32 may be configured to simply detect existence of a fatigue event (i.e., without quantifying the event) based on the scanned image of the operator. And based on existence of the event, immediately initiate the level 2 and/or 3 warnings and/or activate penalty device 36. Other control strategies may also be possible.

It is contemplated that system 26 may be the combination of a fatigue based system with an existing alerter system, if desired. For example, the existing alerter system may function based solely on the frequency of input received from the operator until after system 26 visually detects some minimum level of fatigue in the operator. In this embodiment, system 26 may affect operation of the conventional alerter system only after the minimum level of fatigue is detected. And when the minimum level of fatigue is detected, system 26 may immediately initiate a maximum level of audio and/or visual warning. This could help to snap the operator out of the normal fatigue cycle observed aboard train locomotives equipped with conventional alter systems. It is also contemplated that the audio and/or visual warning implemented based on fatigue detection could be different than the warning normally implemented by the existing alerter systems (e.g., a different volume, sound, etc.).

It is further contemplated that the disclosed system 26 could be associated with a train locomotive event recorder (not shown). For example, each time that a warning is issued and/or when penalty device 36 is activated, the corresponding faults could be logged into the event recorder. This information may then be selectively offloaded from the locomotive to a remote monitoring system, if desired.

Because system 26 may rely on monitored operator activity and also on scanned images of the operator, the system may be more apt to detect and correctly recognize a fatigue event. This improved ability may help to ensure that a response to such events is quickly implemented.

It will be apparent to those skilled in the art that various modifications and variations can be made to the fatigue monitoring system of the present disclosure without departing from the scope of the disclosure. Other embodiments will be apparent to those skilled in the art from consideration of the specification and practice of the fatigue monitoring system disclosed herein. It is intended that the specification and examples be considered as exemplary only, with a true scope of the disclosure being indicated by the following claims and their equivalents.

What is claimed is:

1. A fatigue monitoring system for a machine, comprising:
   an input device configured to generate a first signal indicative of an activity performed by a machine operator;
   a scanning device configured to generate a second signal indicative of a recognized characteristic of the machine operator;
   a warning device; and
   a controller in communication with the input device, the scanning device, and the warning device, the controller configured to:
   determine a time between generations of the first signal;
   make a comparison of the recognized characteristic with a threshold characteristic;
   selectively activate the warning device based on the time or the comparison;
   selectively log a first fault condition and communicate the first fault condition to a central control facility when a penalty device is activated, wherein the penalty device is activated based on the time and the comparison; and
   selectively log a second fault condition when the warning device is activated.

2. The fatigue monitoring system of claim 1, wherein the activity includes a control activity associated with an operation of the machine.

3. The fatigue monitoring system of claim 1, wherein the activity is associated with only resetting of the fatigue monitoring system.

4. The fatigue monitoring system of claim 1, wherein the recognized characteristic is a facial characteristic.

5. The fatigue monitoring system of claim 4, wherein the facial characteristic is one of an eyelid position, an eye blink frequency, and a head pose.

6. The fatigue monitoring system of claim 1, wherein:
   the scanning device is an IR camera disposed within a cabin of the machine; and
   the fatigue monitoring system further includes at least one IR source also disposed within the cabin of the machine.

7. The fatigue monitoring system of claim 1, wherein the warning device is one of a visual warning device and an audible warning device.

8. The fatigue monitoring system of claim 7, wherein:
   the warning device is an audible warning device; and
   the fatigue monitoring system further includes a visual warning device.

9. The fatigue monitoring system of claim 1, wherein the penalty device includes a brake of the machine.

10. The fatigue monitoring system of claim 9, wherein the controller is further configured to selectively reduce throttling of the machine when the brake of the machine is activated as a penalty.

11. The fatigue monitoring system of claim 8, wherein the controller is configured to:
    rate a fatigue level of the machine operator based on the comparison; and
    selectively activate the visual warning device when the fatigue level is a first level or the time between generations of the first signal exceeds a first threshold level.

12. The fatigue monitoring system of claim 11, wherein the controller is further configured to selectively activate the audible warning device when the fatigue level is a second level or the time between generations of the first signal exceeds a second threshold level greater than the first threshold level.

13. The fatigue monitoring system of claim 11, wherein the controller is further configured to selectively activate the penalty device when the fatigue level is a third level or the time between generations of the first signal exceeds a third threshold level greater than the second threshold level.

14. A fatigue monitoring system for a machine, comprising:
    an input device configured to generate a first signal indicative of an activity performed by a machine operator;
    a scanning device configured to generate a second signal indicative of a recognized characteristic of the machine operator;
    a warning device; and
    a controller in communication with the input device, the scanning device, and the warning device, the controller configured to:
    determine a time between generations of the first signal;
    selectively implement a first level response when the time between generations of the first signal exceeds a first threshold time;
    selectively implement a second level response when the time between generations of the first signal exceeds a second threshold time greater than the first threshold time;
    make a comparison of the recognized characteristic with a threshold characteristic;
    selectively implement the second level response based on the comparison;
    selectively log a first fault condition and communicate the first fault condition to a central control facility when a penalty device is activated, wherein the penalty device is activated based on the time and the comparison; and
    selectively log a second fault condition when the warning device is activated.

15. A method of monitoring fatigue of a machine operator, comprising:
    receiving inputs indicative of an activity performed by the machine operator;
    scanning a facial characteristic of the machine operator;
    determining a time between receipt of the inputs;
    making a comparison of the characteristic with a threshold characteristic;
    selectively activating a warning device based on the time or the comparison;
    selectively logging a first fault condition and communicating the first fault condition to a central control facility when a penalty device is activated, wherein the penalty device is activated based on the time and the comparison; and
    selectively logging a second fault condition when the warning device is activated.

16. The method of claim 15, wherein the activity includes one of a control activity associated with machine operation and a resetting activity.

17. The method of claim 15, further including selectively affecting machine braking or fueling based on the time and the comparison.

* * * * *